United States Patent [19]
Lévesque et al.

[11] Patent Number: 6,128,092
[45] Date of Patent: Oct. 3, 2000

[54] METHOD AND SYSTEM FOR HIGH RESOLUTION ULTRASONIC IMAGING OF SMALL DEFECTS OR ANOMALIES.

[75] Inventors: Daniel Lévesque, Terrebonne; Alain Blouin, Montréal; Christian Néron, Boucherville; Jean-Pierre Monchalin, Montréal, all of Canada

[73] Assignee: National Research Council of Canada, Ottawa, Canada

[21] Appl. No.: 09/353,018

[22] Filed: Jul. 13, 1999

[51] Int. Cl.$^7$ ...................................................... G01B 9/02
[52] U.S. Cl. ...................... 356/432 T; 356/345; 356/349
[58] Field of Search ................................. 356/347, 432 T, 356/349, 359, 345

[56] References Cited

U.S. PATENT DOCUMENTS

5,994,690  11/1999  Kulkarnietn ............................. 356/347

Primary Examiner—Robert H. Kim
Attorney, Agent, or Firm—Juliusz Szereszewski

[57] ABSTRACT

A method and system is provided for enhanced ultrasonic detection and imaging of small defects inside or at the surface of an object. The Synthetic Aperture Focusing Technique (SAFT) has been used to improve the detectability and to enhance images in conventional ultrasonics and this method has recently been adapted to laser-ultrasonics. In the present invention, an improved version of the frequency-domain SAFT (F-SAFT) based on the angular spectrum approach is described. The method proposed includes temporal deconvolution of the waveform data to enhance both axial and lateral resolutions, control of the aperture and of the frequency bandwidth to improve signal-to-noise ratio, as well as spatial interpolation of the subsurface images. All the above operations are well adapted to the frequency domain calculations and embedded in the F-SAFT data processing. The aperture control and the spatial interpolation allow also a reduction of sampling requirements to further decrease both inspection and processing times. This method is of particular interest when ultrasound is generated by a laser and detected by either a contact ultrasonic transducer or a laser interferometer.

34 Claims, 6 Drawing Sheets

METHOD AND SYSTEM FOR HIGH RESOLUTION ULTRASONIC IMAGING OF SMALL DEFECTS OR ANOMALIES.

BACKGROUND OF THE INVENTION

1. Field of the Invention

This invention relates to a method and a system for ultrasonic detection and imaging of small defects inside or at the surface of an object by an improved version of the Synthetic Aperture Focusing Technique, and particularly to such method where ultrasound is generated by a laser and detected by either a contact ultrasonic transducer or a laser interferometer.

2. Description of Prior Art

Ultrasound is a well-recognized technique for finding defects or discontinuities in objects. Ultrasound provides not only information on the presence of such discontinuities, but also an indication on their depth, deduced from the arrival time of the echoes and the knowledge of the elastic wave velocity. By scanning the surface with a piezoelectric transducer, the object can be mapped out throughout its entire volume and the information displayed as B-scans or C-scans. B-scans are planar cuts through the material and indicate directly the depth of the discontinuities that are found. C-scans are more like views from the surface and provide depth information by using a color or gray scale code. The coding may be associated either to the arrival time of echoes or their amplitude. Ultrasound can also be used to find flaws at the surface of objects by using waves propagating at their surface (surface or Rayleigh waves) or when the object is a thin plate by using Lamb waves.

Figure 1A:
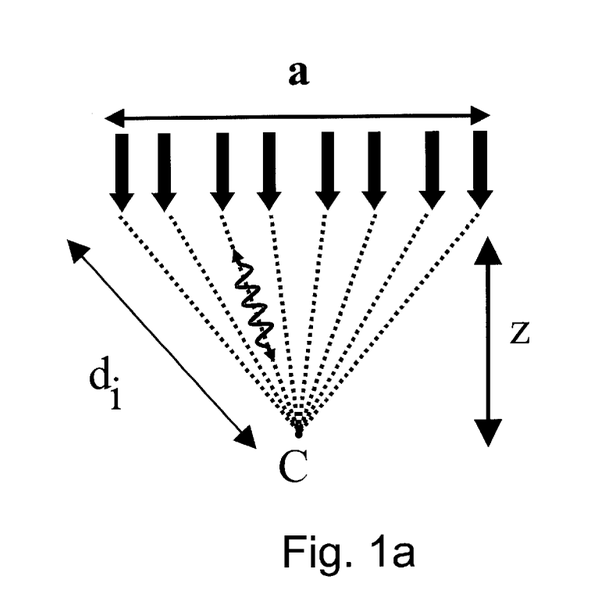
FIG. 1a) is a schematic diagram showing the collection of an array of ultrasonic signals at the sample surface for its use with SAFT known in the prior art, FIG. 1b) is a schematic illustration of a prior art laser-ultrasonic system.

High-resolution imaging and a better definition of the defects are obtained by focusing ultrasound with acoustic lenses or curved transducers. Alternatively, instead of physically focusing ultrasound inside the object (or at its surface), a numerical focusing technique, called Synthetic Aperture Focusing technique (SAFT), can be advantageously used. SAFT allows a lens with a very large effective aperture to be realized numerically, which leads in turn to improved resolution. SAFT has also the advantage of being more easily applicable to objects with complex shapes, once the object contour is known and does not require the realization of a special transducer adapted to the shape of the object. SAFT is implemented by providing a small ultrasonic source at the object surface with a focused transducer and scanning this source over the surface. As shown in FIG. 1a, detection is usually performed at the same location as generation (other schemes are possible) resulting in a 2-D array of signals. SAFT performs a summation of N signals shifted in time and taken from the measurement grid within a given aperture (the synthetic aperture). The time shift of each signal is a function of the point where the signal is collected and the point at a depth z where the presence of a defect is to be determined. The coherent summation increases the SNR for defect detection by the factor $\sqrt{N}$. While maintaining the axial or depth resolution $\Delta z$, the SAFT processing improves the lateral resolution $\Delta x$. It can be shown that the depth and lateral resolutions for defect sizing are given by:

$$\Delta x = \frac{z}{a} v \Delta t \quad \Delta z = \frac{1}{2} v \Delta t \tag{1}$$

where v is the ultrasonic wave velocity, $\Delta t$ is the ultrasonic pulse duration and a is the dimension of the synthetic aperture. Examples of implementation of SAFT can be found in U.S. Pat. Nos. 4,841,489 (Osaki et al.) and 5,465, 722 (Fort et al.). See also the discussions in S. R. Doctor, T. E. Hall, L. D. Reid, "SAFT—the evolution of a signal processing technology for ultrasonic testing", NDT International, 19, 163 (1986) and J. A. Seydel, "Ultrasonic synthetic aperture focusing techniques in NDT", in Research Techniques in Nondestructive Testing Vol. 6, R. S. Sharpe, Ed. NY: Academic, 1983.

Figure 1B:
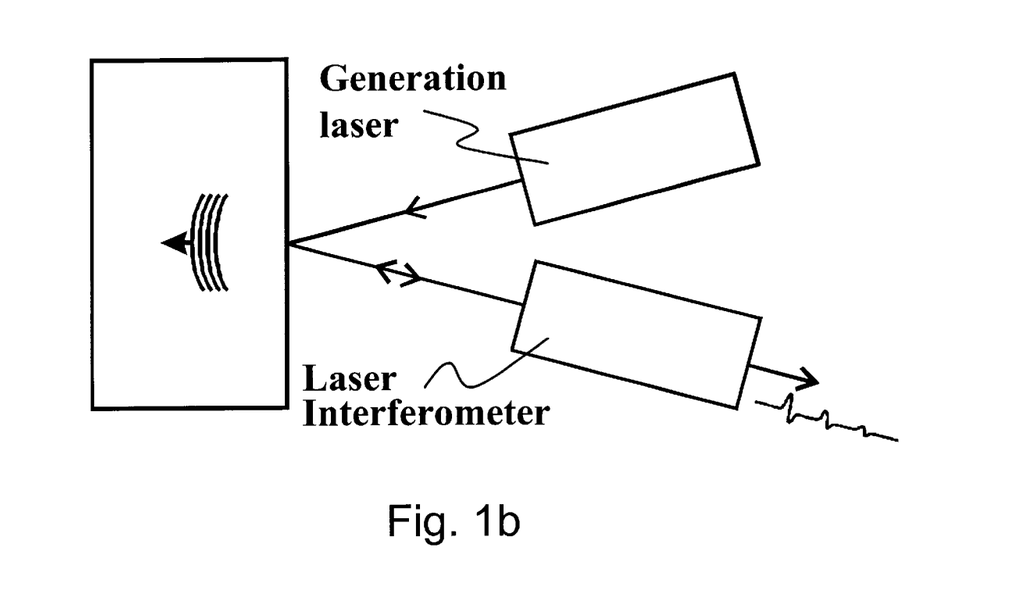

SAFT can also be advantageously applied when using lasers for the generation and detection of ultrasound (a technique called laser-ultrasonics). Laser-ultrasonics uses one laser with a short pulse for generation and another one, long pulse or continuous, coupled to an optical interferometer for detection (see FIG. 1b). Details about laser-ultrasonics can be found in C. B. Scruby, L. E. Drain, "Laser-ultrasonics: techniques and applications", Adam Hilger, Bristol, UK 1990 and J.-P. Monchalin, "Optical detection of ultrasound," IEEE Trans. Ultrason. Ferroelectr. Freq. Control, 33, 485 (1986). By relying on optics for providing the transduction of ultrasound, laser-ultrasonics brings practical solutions for testing at a large standoff distance, for inspecting moving parts on production lines and inspecting in hostile environments (for example, see J.-P. Monchalin et al., "Laser-Ultrasonics: From the Laboratory to the Shop Floor", Advanced Performance Materials, vol. 5, pp. 7–23, 1998). Generation of ultrasound can be performed either in the ablation or thermoelastic regime. In the first case, a sufficiently strong laser pulse provides vaporization or ablation of the surface. The recoil effect following material ejection off the surface produces strong longitudinal wave emission. In the thermoelastic regime, the emission pattern depends on the penetration of light below the surface, which could range typically from microns to hundreds of microns in the case of polymers to practically no penetration in the case of metals. Penetration produces a buried source and a constraining effect that also favors longitudinal ultrasonic emission. In all cases, shear waves are also emitted. When the source is small (smaller than the acoustic wavelength) a complex pattern of emission is obtained, having in some cases several emission lobes. It should be noted that with laser generation, the ultrasonic source is located at the surface of the part and follows automatically the contour. Regarding optical detection, the small phase or frequency shift in the scattered light induced by the ultrasonic surface motion is detected by an interferometric system. For applications where the inspected part is scanned or is moving, a detection scheme that is independent of the speckle or integrates over the whole speckle field is needed. A passive approach based on time-delay interferometry may be used or one can rely on an active one using nonlinear optics for wavefront adaptation. Examples include those discussed in U.S. Pat. Nos. 4,659,224 (Monchalin), 4,966,459 (Monchalin), 5,137,361 (Heon et al.), 5,131,748 (Monchalin et al.) and 5,680,212 (Blouin et al.).

For the detection of small defects, laser-ultrasonics has similar limitations to conventional piezoelectric-based ultrasonics, caused by the wave nature of the interrogation and diffraction effects. The spatial resolution of laser-ultrasonics depends upon the spot sizes of the generation and detection lasers and may be inadequate for detecting small and deep flaws. The use of a broad laser spot to produce an ultrasonic beam with little divergence gives a resolution essentially limited by the spot size. In the opposite case, focusing the laser beam to a small laser spot yields a strongly diverging acoustic wave, leading also to poor resolution. Similarly to conventional ultrasonics, SAFT can be used in conjunction with laser-ultrasonics to improve resolution. Examples of implementation can be found in U.S. Pat. Nos.

5,615,675 (O'Donnell et al.) and 5,801,312 (Lorraine et al.). However the technique described in these two patents presents several difficulties which limit their applicability. A first difficulty originates from the fact that lasers have usually relatively low repetition rates, usually much lower than piezoelectric transducers, which makes data acquisition time very long, so a way to minimize data acquisition duration while maintaining adequate resolution is desirable. A second difficulty is the long time taken by SAFT processing with the time domain approach used in these two patents. This approach is the one that has been explained above. This time domain approach, while straightforward in its principle and implementation, is not very efficient and is very computation intensive. A simple analysis reveals that the processing time scales as $n^5$ for a cubic data block, with n being the number of data points along each axis. A third difficulty originates from the ultrasonic pulse produced by laser generation. This pulse has a unipolar shape so it does not provide destructive interference at locations without defects, resulting in a broad background around discontinuities. As indicated in the Lorraine's patent, this problem was solved by filtering the low frequency components of the waveform data to restore a bipolar pulse shape suitable for use with SAFT. Considering that high spatial resolution relates to a short pulse duration (see equation 1) or a large frequency bandwidth, filtering the low frequency components does not appear to be optimal.

To solve the second difficulty just mentioned, i.e. to improve computational efficiency, SAFT can be implemented in the frequency domain where advantage is taken of the fast Fourier transform (FFT) algorithms. Data processing is performed in the 3-D Fourier space using the angular spectrum approach of the scalar diffraction theory. The use of this method has been reported by K. Mayer, R. Marklein, K. J. Langenberg and T. Kreutter, "Three-dimensional imaging system based on Fourier transform synthetic aperture focusing technique", Ultrasonics 28, 241 (1990) and L. J. Busse, "Three-dimensional imaging using a frequency-domain synthetic aperture focusing technique", IEEE Transactions UFFC 39, 174 (1992). Even with improved computation efficiency, the known frequency-domain method does not provide a clue on how to get optimum resolution. A way to control the aperture size is also missing, which is significant since the strength of the ultrasonic wave and the detection sensitivity both decrease as the lateral distance between the sampling point and the observation point increases and adding contributions from highly offset points contributes more noise than signal. This is straightforward in the time-domain SAFT, but not in the frequency-domain SAFT. This control is particularly important for laser-ultrasonics and in practice, the total opening angle of the synthetic aperture is expected to be limited to roughly 60° when longitudinal waves produced by an ablation or constrained source mechanism are used, which means a~z in equation (1). When shear waves are used, the aperture should be annular. Also, previous art related to SAFT processing does not teach how to minimize the number of sampling points in order to minimize both data collection and processing durations, while keeping adequate resolution.

It is an object of the present invention to provide a method that alleviates the afore-mentioned limitations in the prior art.

SUMMARY OF THE INVENTION

According to the present invention there is provided a method for imaging small defects or anomalies of a target object with a synthetic aperture ultrasonic imaging system wherein ultrasound is generated at a plurality of scanning positions constituting a measurement grid at the surface of the target object, backscattered ultrasound from the measurement grid is detected to provide an array of electrical signals which are digitally sampled, and a Fourier transform is performed on the array of signals in the time domain to generate a new array of signals as a function of the temporal frequency f. Each signal of the new array is deconvolved with a reference signal to obtain an array of broadband deconvolved signals corresponding to spike-like signals in the time domain, an image in real object space at depth z is derived from said deconvolved broadband signals, and the image is displayed to show any defect or anomaly present at depth z.

Preferably, the image is derived by performing a Fourier transform on the resulting new array of signals in the space domain to generate an array in 3D Fourier space with components as a function of the temporal frequency f and spatial frequencies $\delta_x$, and $\delta_y$; the 3-D Fourier space array is backpropagated from the surface of the target object to a plane at depth z within the target object to generate a new array in the 3-D Fourier space; the temporal frequency components are summed over a given bandwidth to generate a new array in 2-D Fourier space corresponding to the plane at depth z; and the new array in 2-D Fourier space is Fourier transformed back to the real object space corresponding to the plane at depth z.

In accordance with another aspect of the invention there is provided a system for ultrasonic imaging small defects or anomalies of an object comprising generating means for generating a small ultrasonic source at a given location on the surface of the object, detecting means for detecting the backscattered ultrasound and providing an electrical signal representative of the ultrasonic motion at the detection location, means for digitizing said electric signal, scanning means for creating a measurement grid at the surface of the object and providing an array of said electrical signals, and processing means for performing a Fourier transform on the array of signals recorded at said measurement grid, wherein the processing means deconvolves the transformed signals with a reference signal to create a new array of signals which are used to derive an image in real object space at depth z, and display means are provided for displaying the subsurface image to show object boundaries and any defect present at a depth z.

BRIEF DESCRIPTION OF THE DRAWINGS

The invention will be described in more detail, by way of example only, with reference to the accompanying drawings, in which.

DETAILED DESCRIPTION OF THE PREFERRED EMBODIMENTS OF THE INVENTION

Figure 2A:
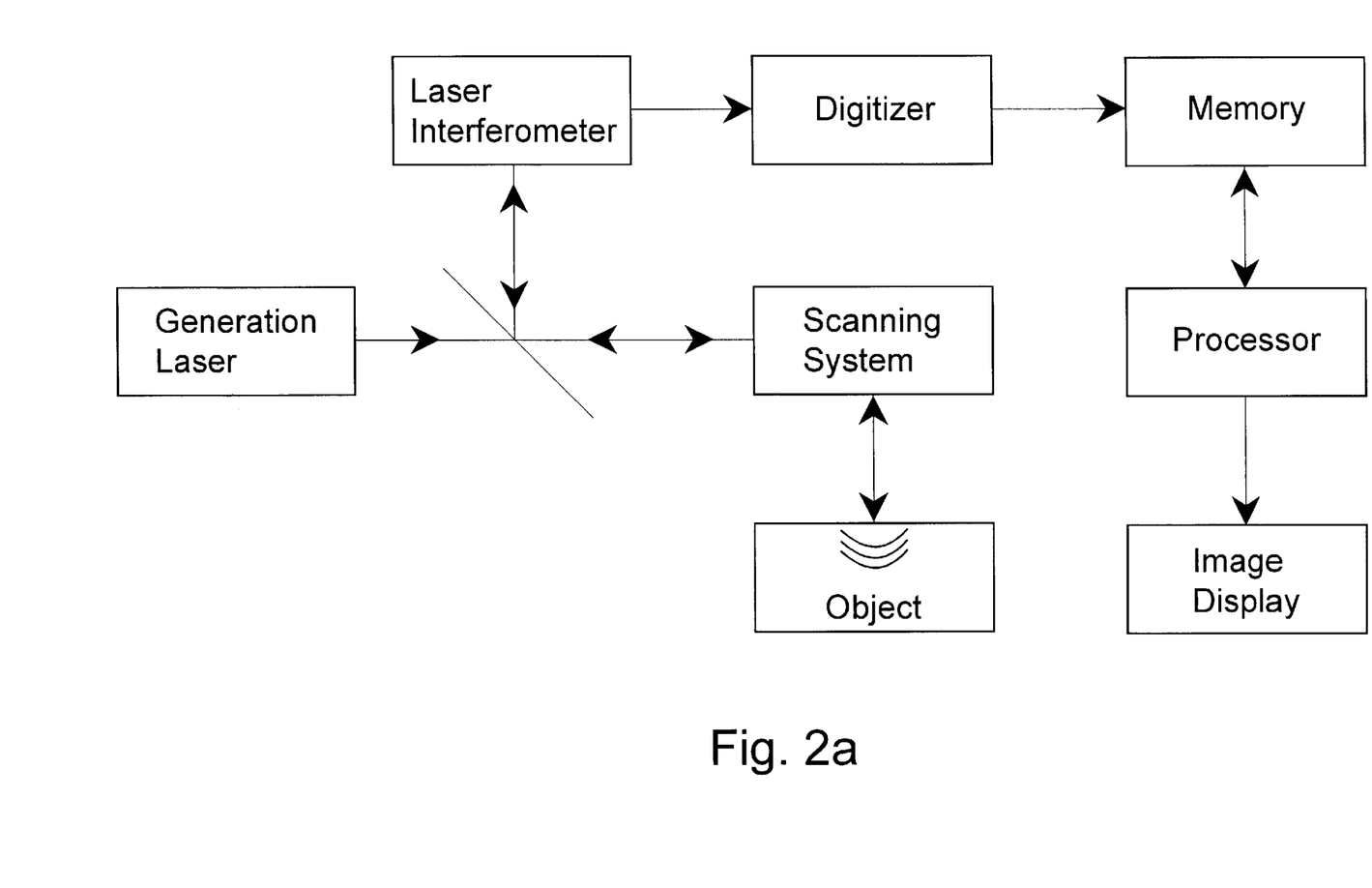
FIG. 2a) is a schematic diagram of a laser-ultrasonic imaging system according to one embodiment of the invention, FIG. 2b) is a block diagram illustrating the various steps of the F-SAFT method, FIG. 2c) illustrates reconstruction speed of F-SAFT for a cubic data block of size n.

Referring now to FIG. 2a the system according to one preferred embodiment comprises a laser ultrasonic system collecting a 2-D array of ultrasonic signals at the surface of the sample for imaging small defects at its inside. The generation laser 10 is a pulsed laser source and the laser interferometer 12 for detecting backscattered ultrasound comprises a long pulse laser or continuous laser coupled to an optical interferometer. The two laser beams for generation and detection, are focused at the same location onto the surface in a manner similar to the arrangement shown in FIG. 1b. A scanning system 14 is employed for generating and detecting ultrasound at a plurality of scanning positions constituting the measurement grid at the surface of the object 16. In the present embodiment, the array of signals is obtained by scanning the beams on the sample surface with steered mirrors. Alternatively, the sample could be moved using an X-Y translation table. Preferably, the measurement grid has constant step sizes, $\delta x$ and $\delta y$, in both the x and y directions. The backscattered signal detected at each scanning position on the measurement grid is digitally sampled by a digitizer 18, which uses oversampling to better estimate each temporal frequency component, and stored into a memory 20, thus providing an array of waveform data. A processor unit 22 comprising a single or several processors is used for SAFT reconstruction and generation of the subsurface images using the method described below. The images are displayed by a display unit 24.

Other embodiments where the two laser beams are offset from each other or are not simultaneously scanned can also be easily implemented. With prior knowledge of the part shape, this laser-ultrasonic imaging system can also be applied to samples with non-planar front surfaces.

Figure 2B:
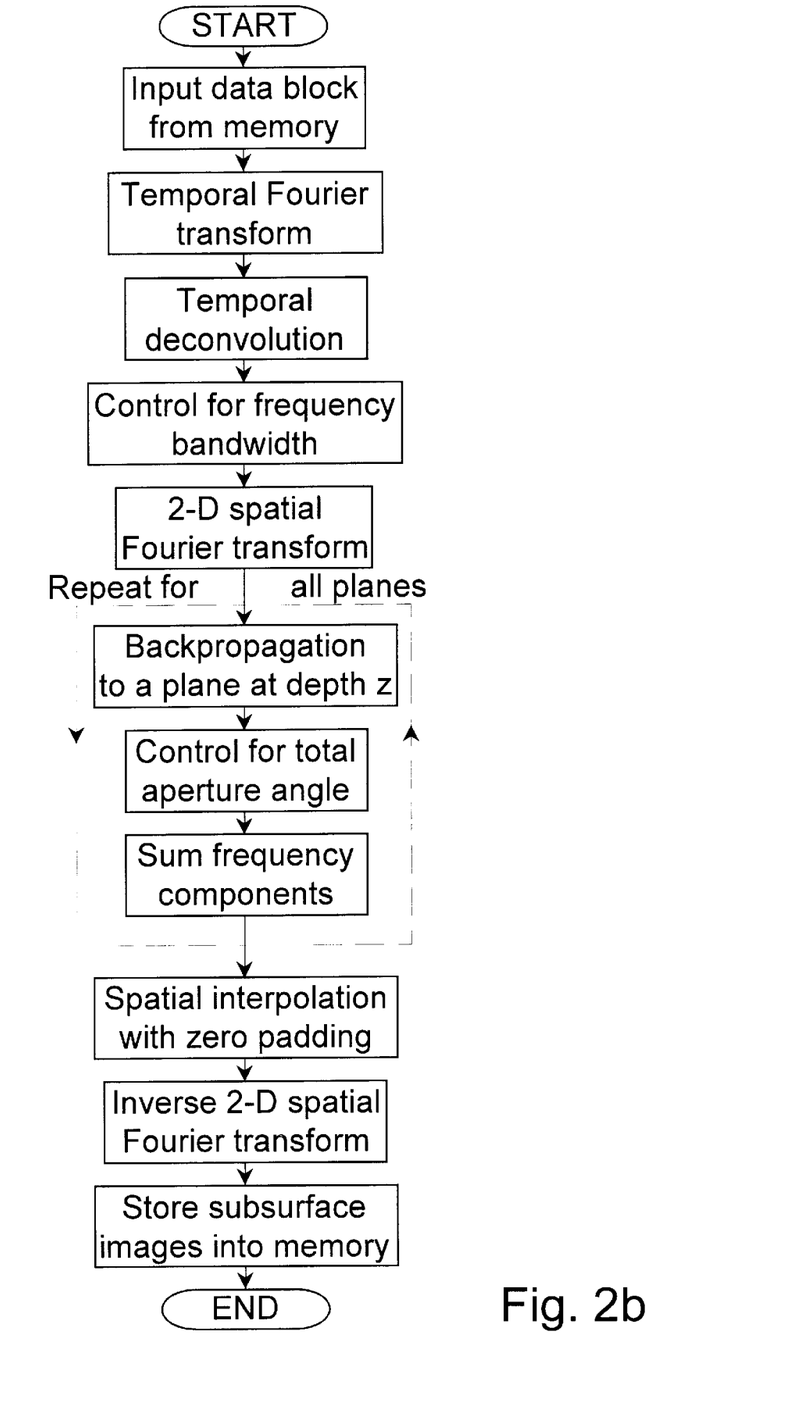

The method of the present invention (called below F-SAFT) is based on processing data in Fourier space and provides significant improvements over previous frequency-domain SAFT methods. The method can be used advantageously with either a conventional piezoelectric-based ultrasonic system or the preferred laser-ultrasonic imaging system described above. FIG. 2b shows an example of implementation of the proposed method and the various steps it comprises.

Starting from the acoustic field $S(x,y,z=0,t)$ at the sample surface of the measurement grid, a 3-D Fourier transformation is first performed with respect to variables (x, y, t) into a 3-D Fourier space represented by variables $(\delta_x, \delta_y, f)$. Physically, these transformations can be seen as if the acoustic field of frequency f is represented by a superposition of plane waves at different angles with spatial frequencies $\delta_x, \delta_y$. Then, the transformed field $\bar{S}(\delta_x, \delta_y, z=0, f)$ is backpropagated to any depth z using the expression:

$$\bar{S}(\delta_x, \delta_y, z, f) = \bar{S}(\delta_x, \delta_y, 0, f) \exp(\pm 2\pi i z \sqrt{2f/v)^2 - \delta_x^2 - \delta_y^2}) \quad (2)$$

with ± corresponding to the sign of f and summed over the temporal frequencies as follows:

$$\overline{\Sigma}(\sigma_x, \sigma_y, z) = \sum_{f \in \Omega} \bar{S}(\sigma_x, \sigma_y, z, f) \quad (3)$$

where $\Omega$ is the selected frequency bandwidth including negative components. Finally, after to addition of zero values, an inverse 2-D Fourier transformation of $\overline{\Sigma}(\delta_x, \delta_y, z)$ with respect to variables $(\delta_x, \delta_y)$ is performed, yielding the space domain function $\Sigma(x,y,z)$. The back propagation and summing of temporal frequency components is performed for a plurality of planes corresponding to different depths within the object.

A flaw is present at position x, y and z if the function $\Sigma$ at this point exhibits a peak. It is worth mentioning that windowing and smoothing techniques can be applied either in the time or frequency domain prior to any of the above Fourier transformations. For a cubic data block, the algorithm is found to scale as $n^4$ for computing equations (2) and (3), and as $n^3 \log n$ for Fourier transformations using a FFT (Fast Fourier Transform) algorithm. Therefore, the frequency-domain SAFT method is inherently faster than conventional time domain SAFT for moderately large values of n.

Figure 2C:
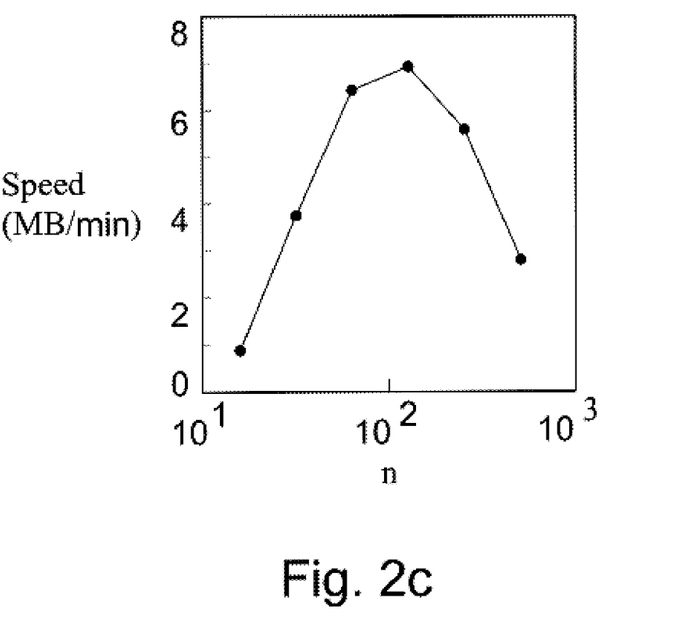

FIG. 2c shows the actual reconstruction speed obtained for different values of n on a PC Pentium II 400 MHz. The speed is defined here as the reciprocal of processing time (in min) divided by the size of the corresponding data block (in Mbytes, 16 bits per data points). The performance on this machine appears optimal for the size n=128, with a reconstruction speed of 7 MB/min. It is worth mentioning that for inspection over a large area, the reconstruction can be made on many overlapping data blocks.

Figure 3A:
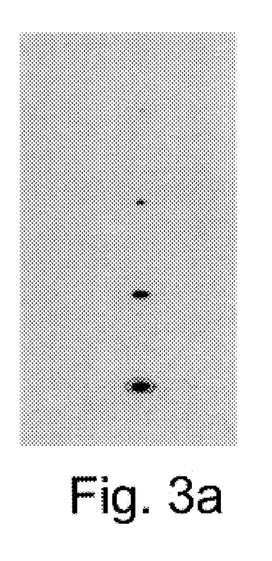
FIG. 3a) illustrates a signal amplitude C-scan.
Figure 3B:
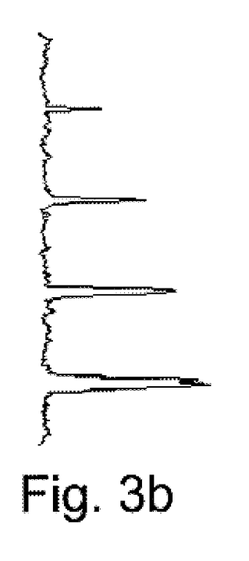
FIG. 3b) illustrates a signal amplitude profile.
Figure 3C:
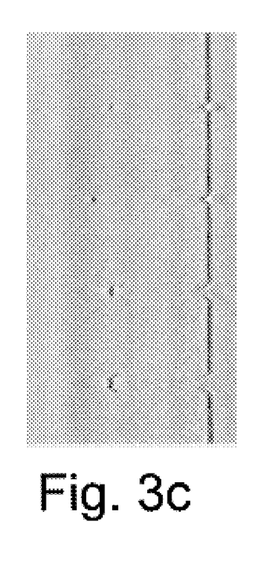
FIG. 3c) illustrates a B-scan of F-SAFT processed data from a test specimen.

Although computationally efficient, the known frequency-domain method can be significantly improved to get very high resolution images of small defects and overcome the limitations mentioned when using laser-ultrasonics. FIG. 3 shows the results from the improved version of frequency-domain SAFT (called F-SAFT) on laser-ultrasonic data obtained on a test specimen made from an aluminum block 7 mm thick. All the key features of the proposed F-SAFT method discussed next were used, except spatial interpolation. To simulate buried flaws, four flat-bottom holes, 10 mm apart, approximately 2 mm deep and of diameter 1.5, 1.0, 0.5 and 0.34 mm were drilled on the back surface of a sample object. In the present embodiment, the generation laser was a short pulse ($\approx 5$ ns) Q-switched Nd:YAG laser operating on its fourth harmonic. Generation of ultrasound was performed in the ablation regime. A single mode, highly stable, long pulse (50 $\mu$s) Nd:YAG laser operated on its fundamental wavelength of 1.064 µm was used for detection of ultrasound. The light of the detection laser scattered off the surface sample was sent to a confocal Fabry-Perot interferometer operated in reflection mode (length of 1 m and mirror reflectivities of 89%). The frequency bandwidth of the system extended from 1 to 35 MHz. The two laser beams were focused onto the surface of the specimen at about the same location. The generation and detection spot sizes were 0.1 mm and 0.3 mm, respectively. The step size of the scan was 0.1 mm and the inspected area was 12.5×45 mm. For each node of the measurement grid, an ultrasonic signal was collected, digitized and stored in the computer memory. The whole block of data was then processed by the F-SAFT method.

FIGS. 3a, 3b and 3c show an amplitude C-scan and a B-scan of the processed data after reconstruction at depths from 3 to 7.5 mm with a step size of 0.05 mm. To evaluate the SNR, a profile extracted from the C-scan along a line crossing the holes is also shown in FIG. 3. The laser-ultrasonic F-SAFT imaging provides very good detection of all the 5-mm deep defects, with a SNR ranging from 24 dB for the 0.34-mm hole to 33 dB for the 1.5-mm hole. The lateral resolution of the flat-bottom holes is also found to be excellent. The apparent diameters (width at half maximum of the profile) of the 0.34-mm and 1.5-mm diameter holes are 0.4 mm and 1.6 mm, respectively.

Figure 4A:
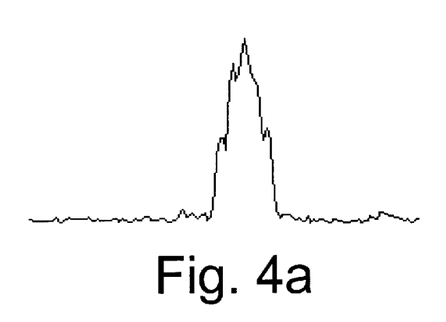
FIG. 4a) illustrates profiles at the top of the 1.5 mm flat-bottom hole after F-SAFT processing without deconvolution, FIG. 4b) illustrates similar profiles as FIG. 4a but including deconvolution.
Figure 4B:
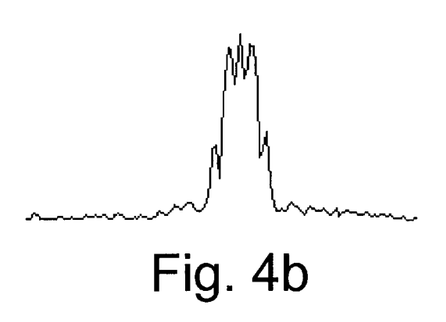

A first feature indicated in FIG. 2b of the exemplary F-SAFT method is the temporal deconvolution of the ultrasonic waveform data. The effect of deconvolution is to replace the ultrasonic pulses by spike-like pulses. Therefore, the ultrasonic pulse duration, Δt, is reduced and consequently both depth and lateral resolutions are improved, as indicated by equation (1). Preferably, Wiener deconvolution is used in the method and is well adapted to the frequency domain calculations. Each signal $\overline{S}(x,y,f)$ at the sample surface of the measurement grid is substituted by the function $\overline{H}(x,y,f)$, given by:

$$\overline{H}(x, y, f) = \overline{S}(x, y, f) \left[ \frac{\overline{R}(f)^* e^{2\pi i f \tau}}{|\overline{R}(f)|^2 + \chi^2 |\overline{R}(f)|^2_{\max}} \right] \quad (4)$$

where $\overline{R}(f)$ is the reference pulse, τ is the time delay required to shift the reference pulse at time t=0 and χ is a user-specified constant used to quantify noise in the signal. Notice that the symbol "*" denotes complex conjugate and the subscript "max" denotes the maximum value. The value of user-specified constant χ, usually between 0.02 and 0.2, has to be carefully chosen to avoid the deterioration of the SNR while trying to improve the resolution. The reference pulse used in the data given as example is the backwall reflection echo. Note that the bracket in equation (4) is a vector that has to be evaluated only once so this operation has only minor effects on processing time. Two other benefits of deconvolution are an improved precision in the location of defects due to a more symmetric pulse shape of the deconvolved signal and an accurate determination of the time origin when the reference pulse is selected from the data block, due to the self-referencing of the deconvolution at t=0. The performance of this feature of the F-SAFT method is shown in FIGS. 4a and 4b. As shown in these figures, the flat top shape of the 1.5 mm hole is revealed by the method (FIG. 4b) whereas standard frequency-domain SAFT does not provide similar information (FIG. 4a).

A second feature of the F-SAFT method is the control of the frequency bandwidth of reconstruction. With respect to equation (3), the frequency bandwidth control can be achieved by limiting the sum to the actual frequency bandwidth of the ultrasonic inspection system, Ω. Embedded in the F-SAFT processing, this control is very effective and make any pre-filtering of the ultrasonic signals unnecessary, as it would be required using time-domain SAFT. This frequency bandwidth control results in a reduced processing time and an increase of the SNR, since noise contribution from high frequency components without ultrasonic information are removed. The advantage of oversampling during acquisition to better estimate each frequency components within Ω is also preserved.

A third feature of the F-SAFT method consists in controlling the aperture in the frequency domain. As already mentioned, the transformation to the 3-D Fourier domain can be seen as representing the acoustic field of frequency f by a superposition of plane waves at different angles with spatial components $\delta_x, \delta_y$. The direction cosines of the wave components are related to the orientation of the wave vector $\hat{k}$ with respect to the coordinate axes. Therefore, the angle of a given plane wave with respect to the z axis is given by:

$$\frac{k_z}{k} = \frac{\sqrt{(2f/v)^2 - \sigma_x^2 - \sigma_y^2}}{2f/v} = \cos\theta_z \quad (5)$$

Figure 5:
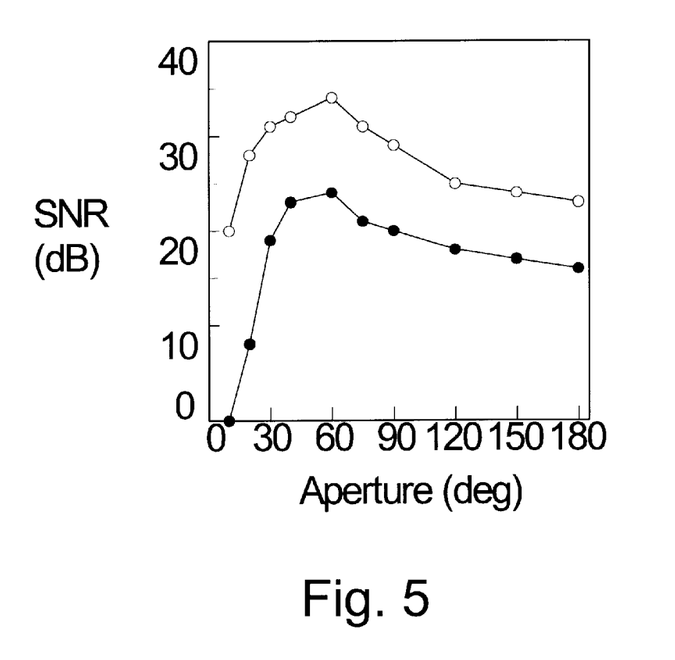
FIG. 5 illustrates influence of the aperture on the SNR after F-SAFT reconstruction for the 0.34 mm diameter hole (solid circles) and the 0.5 mm diameter hole (open circles) of the test specimen.

It will be observed that for simultaneously scanned generation and detection, the acoustic propagation distances are doubled and this is accounted for by the factor 2 appearing with the wave vector in equations (2) and (5). Since it is expected that there is little signal at large values of $\theta_z$, because of a decrease of wave emission and detection sensitivity at these values, one should limit $\theta_z$ to a maximum value θ to avoid the addition of noise, i.e. cos $\theta_z$>cos θ. It then follows a condition on the temporal frequencies f to be included in the summation of equation (3):

$$\frac{v}{2} \frac{\sqrt{\sigma_x^2 + \sigma_y^2}}{\sin\theta} < f < f_{\max} \quad (6)$$

where $f_{max}$ is the maximum frequency in the bandwidth Ω. For increasing values of the spatial components $\delta_x, \delta_y$, the number of temporal frequency components f used in the summation is progressively reduced. Note that for a total opening angle of 180°, eq. (6) automatically excludes the contribution from evanescent waves by restricting the argument in the exponential function of eq. (2) to be imaginary. The influence of the aperture on SNR for the 0.34-mm and 0.5-holes is shown in FIG. 5 for the test specimen described above. The SNR rapidly increases with aperture size, reaches a maximum at around 60° and then progressively decreases, by at least 6 dB, as a result of including components that contribute more noise than coherent signal. In addition, the processing time is reduced since less data points are included in the SAFT processing by proper reduction of the aperture.

A benefit of the aperture control feature of the method is a reduction in spatial sampling requirement. The choice of scanning step size δ (either δx or δy) is a compromise between the smallest detectable defect and the time for inspection and processing. A standard practice is to apply the criterion, $\delta < \lambda_{min}/2$, where $\lambda_{min}$ is the smallest acoustic wavelength which is present or required. With this criterion, propagating waves over an aperture of 2θ=180° as well as evanescent waves are included in the direct and formal use of the angular spectrum approach. However in the application to the F-SAFT method, the control of the aperture limits the angular range over which the plane waves in the expansion contribute. Therefore, the spatial frequencies are limited to a value $\delta_{max}$ (either in the x or y direction) given by eq. (6):

$$\sigma_{max} = \frac{\sin\theta}{\lambda_{min}} \quad (7)$$

where $\lambda_{min}$ is the effective smallest wavelength equal to $v/2f_{max}$. Following Nyquist, adequate sampling requires a scanning step size $\delta$ smaller than $1/(2\delta_{max})$:

$$\delta < \frac{\lambda_{min}}{2}\left(\frac{1}{\sin\theta}\right) \quad (8)$$

Figure 6A:
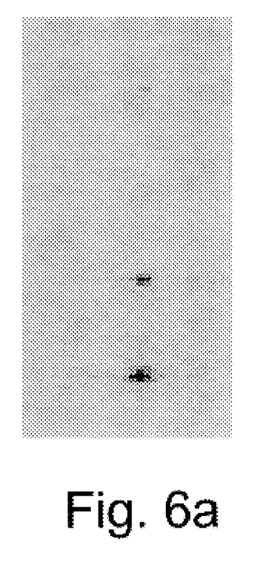
FIGS. 6a) and 6b) illustrate C-scans after F-SAFT reconstruction for two subsets taken from the original grid corresponding to a step size of: 0.4 mm (FIG. 6a) and 0.2 mm (FIG. 6b), FIG. 6c) repeats the C-scan in FIG. 3a obtained from the original grid with step size of 0.1 mm.
Figure 6B:
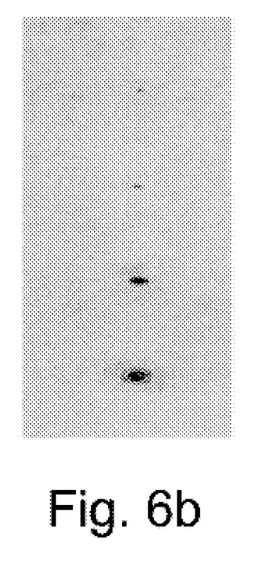
Figure 6C:
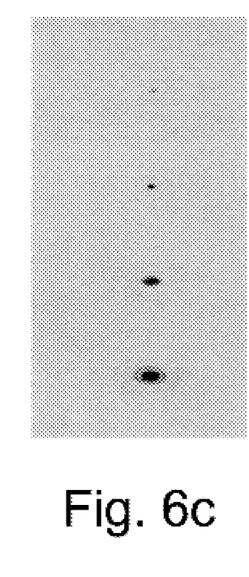

Note that equation (8) reduces to the standard criterion, $\delta<\lambda_{min}/2$, for a total opening angle of $2\theta=180°$. For a nearly optimal aperture of 60°, the sampling requirement is $\delta<\lambda_{min}$, corresponding to a reduction factor of 2 (or 4 for the whole measurement grid) compared to the standard criterion, which allows to decrease both inspection and processing times. If the effective smallest wavelength is set equal to the size of the smallest detectable defect w, then using an optimal aperture, the relation $\delta\sim\lambda_{min}\sim w$ is obtained. For the test specimen described above, this corresponds to a sampling interval of 0.34 mm instead of the 0.1 mm used. To demonstrate this point, two subsets of signals were taken from the original grid of 126×451 signals and were processed by F-SAFT. FIG. 6a shows the C-scan obtained with a subset of 31×112 signals, corresponding to a step of 0.4 mm to be compared with original C-scan obtained with a 0.1 mm step, shown in FIG. 3a and reproduced in FIG. 6c. As expected from the previous argument, the 0.34-mm hole is detected but with a poor SNR of 11 dB. FIG. 6b shows the C-scan obtained with a subset of 63×225 signals corresponding to a step of 0.2 mm. In this case, the smallest 0.34-mm hole is well observed, with a SNR of 21 dB close to the 24 dB obtained with the original 0.1 mm step. The resolution and even SNR may be improved by the interpolation feature as discussed next.

The proposed interpolation feature is well adapted to the frequency domain and directly embedded in the F-SAFT method. For each depth z, the algorithm simply consists in padding the function $\overline{\Sigma}(\delta_x,\delta_y,z)$ with zeros prior to its inverse 2-D Fourier transformation with FFT, yielding the function $\Sigma(x,y,z)$ at intermediate points. This approach is demonstrated with the two subsets discussed above and taken from the original grid.

Figure 7A:
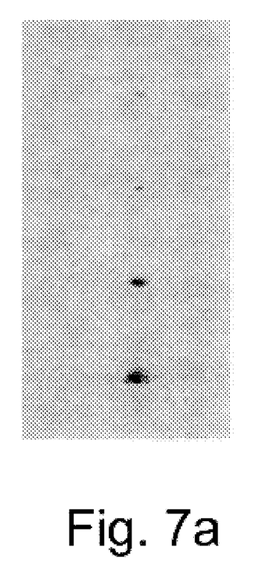
FIGS. 7a) and 7b) represent C-scans after F-SAFT reconstruction for the two subsets of step size 0.4 mm (FIG. 7a) and 0.2 mm (FIG. 7b), and including spatial interpolation to provide information at an interval of 0.1 mm, FIG. 7c) repeats the C-scan in FIG. 3a obtained from the original grid with step size 0.1 mm.
Figure 7B:
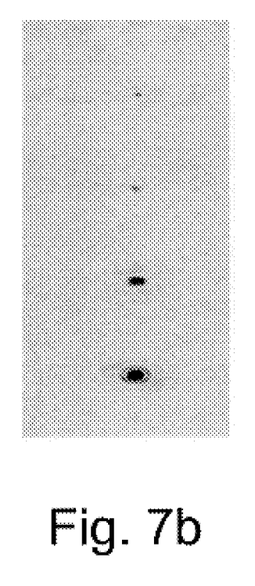
Figure 7C:
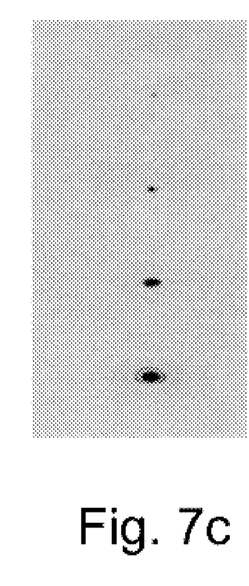

FIGS. 7a and 7b show the C-scans obtained respectively from the 31×112 grid (step size of 0.4 mm) and from the 63×225 grid (step size of 0.2 mm), both including interpolation to provide information at intervals of 0.1 mm. When compared to corresponding FIGS. 6a and 6b, the small 0.34-mm hole indeed appears more clearly using spatial interpolation. However, for the coarser grid in FIG. 7a, the size of the 0.34-mm hole appears overestimated with reference to the 0.5-mm hole, indicative of an imperfect reconstruction. Another indication of critical sampling is the increase of SNR from 11 dB to 16 dB when including interpolation, a SNR which remains unchanged with 21 dB using the finer grid having 0.2 mm step size. Then using a coarser grid, the SNR can be improved by using an interpolation technique since a peak associated with the presence of a defect in the function $\Sigma(x,y,z)$ may be more accurately resolved, with possibly a SNR gain by a factor of 2 corresponding to 6 dB. While less accurate than using the original grid (reproduced in FIG. 7c), the C-scan in FIG. 7a appears quite acceptable, especially if one takes into account the reduction by 16 in the inspection time and nearly by 5 in the processing time.

The proposed method and system can also be readily applied to the detection and imaging of surface defects using either ultrasonic plate (Lamb) waves or surface (Rayleigh) waves. This approach has already been described in the U.S. Pat. No. 5,760,904 (Lorraine and Hewes), but using the less efficient time-domain SAFT. In this case, only a single line scan is required with the system, collecting ultrasonic signals at the sample surface along direction x and imaging small surface defects at various distances from the scanning line along direction z. If the ultrasonic waves are dispersive, i.e. the phase velocity is frequency dependent, this is easily accounted for in F-SAFT by attributing for each temporal frequency during backpropagation to distance z the velocity value at this frequency in eq. (2).

The proposed method and system can also be readily applied to the so-called opto-acoustic imaging used in the medical field to detect anomalies in tissue with enhanced contrast and resolution. The effect is the same as mentioned above for the generation of ultrasound. The interest of the technique and its enhanced contrast originates from the variation of light penetration between various tissues, particularly between sound and cancerous ones. Ultrasound is detected by a contact transducer which is either piezoelectric or based on fiber optics. The approach combines the advantages of optics (better contrast between tissues) and ultrasonics (less scattering during propagation). Details about opto-acoustics can be found in R. A. Kruger et al., "Photoacoustic ultrasound-reconstruction tomography", Med. Phys. 22, 1605–1609 (1995), A. A. Oraevsky et al., "Laser opto-acoustic tomography for medical diagnostics: Principles" R. A Lieberman et al., eds., Proc. SPIE conf. on biomedical sensing, imaging and tracking technologies I, 2676, SPIE Press, Bellingham, Wash., pp. 22–31 (1996). However, for a clinically relevant and viable system, improvements in 2-D detection have to take place using both multiplexed array transducers and a suitable image reconstruction method. For examples, see the recent works from R. O Esenaliev et al., "Laser Optoacoustic imaging for breast cancer diagnostics: Limit of detection and comparison with X-rays and ultrasound imaging", B. Chance and R. R. Alfano, eds., Proc. SPIE conf. on optical tomography and spectroscopy of tissue: Theory, instrumentation, model and human studies II 2979, SPIE Press, Bellingham, Wash., pp. 71–82 (1997) and C.G.A Hoelen et al., "Three-dimensional photoacoustic imaging of blood vessels in tissue", Opt. Lett. 28 (1998). Therefore, this application can benefit from using the above described F-SAFT method and system.

Of course, numerous other than described above embodiments of the method and system may be envisaged without departing from the spirit and scope of the invention.

The embodiments of the invention in which an exclusive property or privilege is claimed are defined as follows:

1. A method for imaging small defects or anomalies of a target object with a synthetic aperture ultrasonic imaging system comprising the steps of:

generating ultrasound at a plurality of scanning positions constituting a measurement grid at the surface of the target object;

detecting ultrasound backscattered from the measurement grid to provide an array of electrical signals which are digitally sampled;

performing a Fourier transform on the array of signals in the time domain to generate a new array of signals as a function of the temporal frequency f;

deconvolving each signal of the new array with a reference signal to obtain an array of broadband deconvolved signals corresponding to spike-like signals in the time domain:

deriving an image in real object space at depth z from said deconvolved broadband signals; and displaying the image to show any defect or anomaly present at depth z.

2. A method as claimed in claim 1, wherein the frequency bandwidth of the deconvolved array is limited to the actual bandwidth of the ultrasonic imaging system.

3. A method as claimed in claim 2, wherein the aperture of the ultrasonic imaging system is controlled in the frequency domain.

4. A method as claimed in claim 3, wherein the image is derived by performing a Fourier transform on the resulting new array of signals in the space domain to generate an array in 3D Fourier space with components as a function of the temporal frequency f and spatial frequencies $\delta_x$ and $\delta_y$; the 3-D Fourier space array is backpropagated from the surface of the target object to a plane at depth z within the target object to generate a new array in the 3-D Fourier space; the temporal frequency components are summed over a given bandwidth to generate a new array in 2-D Fourier space corresponding to the plane at depth z; and the new array in 2-D Fourier space is Fourier transformed back to the real object space corresponding to the plane at depth z.

5. A method as claimed in claim 4, wherein each signal is deconvolved using frequency-domain Wiener deconvolution.

6. A method as claimed in claim 1, wherein said reference signal for temporal deconvolution is a pulse selected from a data block, representative of the ultrasonic excitation source and of its propagation in the target object.

7. A method as claimed in claim 4, wherein the backpropagation of the 3D space array and the summing of the temporal frequency components are performed for a plurality of planes corresponding to different depths z within the object.

8. A method as claimed in claim 4, wherein said electrical signals are oversampled to better estimate each temporal frequency component.

9. A method as claimed in claim 8, wherein said given bandwidth has an upper cut-off to eliminate contributions from high frequency noise.

10. A method as claimed in claim 9, wherein said given bandwidth has a progressive lower cut-off with increasing spatial frequencies to control the angular aperture.

11. A method as claimed in claim 10, wherein spatial sampling on the inspected surface of the object is reduced as claimed in the reduction of the angular aperture.

12. A method as claimed in claim 4, wherein zero values are added prior to performing the Fourier transform back to the real object space.

13. A method as claimed in claim 12, wherein spatial sampling on the inspected surface of the target object is reduced as claimed in the effect of adding points in the space domain by addition of zeroes in the frequency domain.

14. A method as claimed in claim 4, wherein windowing and smoothing techniques are applied either in the time or frequency domain prior to Fourier transformation.

15. A method as claimed in claim 1, wherein the data collected from an inspected surface is partitioned and processed in a plurality of overlapping cubic datablocks of size n, for optimal reconstruction speed.

16. A method as claimed in claim 4, wherein dispersive effects are compensated during backpropagation to depth z, by attributing to each temporal frequency the velocity value at this frequency.

17. A method as claimed in claim 4, wherein the generation and detection of ultrasound is performed at a plurality of scanning positions along a single line for imaging small defects on the surface at various distances z from the scanning line using either Lamb waves or Rayleigh waves.

18. A method as claimed in claim 17, wherein dispersive effects are compensated for during backpropagation to distance z from the line scan by attributing to each temporal frequency the velocity value at this frequency.

19. A method as claimed in claim 1, wherein the ultrasound is generated by a laser.

20. A system for ultrasonic imaging small defects or anomalies of an object comprising:

an ultrasound generator for generating a small ultrasonic source at a given location on the surface of the object;

a detector for detecting the backscattered ultrasound and providing an electrical signal representative of the ultrasonic motion at the detection location;

a digitizer for digitizing said electric signal;

a scanner for creating a measurement grid at the surface of the object and providing an array of said electrical signals;

a processor for performing a Fourier transform on the array of signals recorded at said measurement grid, deconvolving the transformed signals with a reference signal to create a new array of signals, and deriving from the new array an image in real object space at depth z; and a display for displaying the subsurface image to show object boundaries and any defect present at a depth z.

21. A system as claimed in claim 20, wherein said processor further backpropagatess the new array from the surface of the object to a depth z within the object, sums the temporal frequency components over a given bandwidth, and performs a Fourier transform on the new array back to real object space to obtain the subsurface image at depth z.

22. A system as claimed in claim 21, wherein the processor backpropagates and sums the temporal frequency components for a plurality of planes corresponding to different depths z within the object.

23. A system as claimed in claim 22, wherein the digitizer oversamples the electrical signal to better estimate each temporal frequency components.

24. A system as claimed in claim 20, wherein said processor performs windowing and smoothing either in the time or frequency domain prior to Fourier transformation.

25. A system as claimed in claim 24, further comprising means for partitioning and processing the data collected from the inspected surface in a plurality of overlapping cubic datablocks of size n, for an optimal reconstruction speed.

26. A system as claimed in claim 21, wherein the processor compensates for dispersive effects during backpropagation to depth z, attributing to each temporal frequency the velocity value at this frequency.

27. A system as claimed in claim 20, wherein the ultrasound generator, detector and scanner means are arranged to be applied to a plurality of positions along a single line for imaging small defects on the surface of the object at various distances z from the scanning line.

28. A system as claimed in claim 21, wherein the processor further compensates for dispersive effects during backpropagation to distance z from the line scan, attributing to each temporal frequency the velocity value at this frequency.

29. A system as claimed in claim 20, wherein the generator is a pulsed laser.

30. A system as claimed in claim 20, wherein the detector is a long pulse laser or a continuous laser coupled to an optical interferometer.

31. A system as claimed in claim 20, wherein the detector is an ultrasonic transducer in contact with the object.

32. A system as claimed in claim 31, wherein the contact ultrasonic transducer uses fiber optics.

33. A computer readable medium containing stored instructions for a computer to perform the method claimed in claim 1.

34. A computer readable medium containing stored instructions for a computer to perform the method claimed in claim 4.

* * * * *

UNITED STATES PATENT AND TRADEMARK OFFICE
CERTIFICATE OF CORRECTION

PATENT NO.    : 6,128,092
DATED         : October 3, 2000
INVENTOR(S)   : Daniel Levesque; Alan Blouin; Christian Neron; Jean-Pierre Monchalin It is certified that error appears in the above-identified patent and that said Letters Patent is hereby corrected as shown below:

Column 4,
Line 20, twice "$\delta$" should be "$\sigma$"

Column 6,
Line 7, "$\delta$" should be "$\sigma$"
Line 11, "$\delta$" should be "$\sigma$"
In the equation, the first two entries: "$\delta$" should be "$\sigma$"
Line 25, "$\delta$" should be "$\sigma$"
Line 26, "$\delta$" should be "$\sigma$"

Equation 3, "$\overline{\overline{\Sigma}}$" should be made smaller "$\overline{\overline{\Sigma}}$"

Column 8,
Line 17, "$\delta$" should be "$\sigma$"
Line 42, "$\delta$" should be "$\sigma$"

Column 9,
Line 3, "$\delta$" should be "$\sigma$"
Line 12, second "$\delta$" only, should be "$\sigma$"
Line 45, "$\delta$" should be "$\sigma$"

Column 11,
Line 19, "$\delta$" should be "$\sigma$"

Signed and Sealed this

Thirtieth Day of October, 2001

Attest:

*Nicholas P. Godici*

NICHOLAS P. GODICI
*Attesting Officer*   *Acting Director of the United States Patent and Trademark Office*